United States Patent
Kinoshita et al.

(10) Patent No.: US 6,359,155 B1
(45) Date of Patent: Mar. 19, 2002

(54) PROCESS FOR THE PREPARATION OF 3-HYDROXYTETRAHYDROFURAN

(75) Inventors: Koichi Kinoshita, Kakogawa; Tadashi Moroshima, Takasago; Yoshifumi Yanagida, Kakogawa; Nobuo Nagashima, Takasago; Yasuhiro Saka, Akashi; Tatsuya Honda; Yoshihide Fuse, both of Kobe; Yasuyoshi Ueda, Himeji, all of (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/719,686

(22) PCT Filed: Apr. 14, 2000

(86) PCT No.: PCT/JP00/02431

§ 371 Date: Feb. 15, 2001

§ 102(e) Date: Feb. 15, 2001

(87) PCT Pub. No.: WO00/63199

PCT Pub. Date: Oct. 26, 2000

(30) Foreign Application Priority Data

Apr. 15, 1999  (JP) ............................................. 11-107398
Jan. 17, 2000  (JP) ......................................... 2000-007994

(51) Int. Cl.⁷ ...................... C07D 307/20; C07C 29/147
(52) U.S. Cl. ......................... 549/475; 568/844; 203/63; 203/64; 203/66
(58) Field of Search ........................ 549/475; 568/844; 203/63, 64, 66

(56) References Cited

U.S. PATENT DOCUMENTS 4,864,046 A   9/1989   Volkmann ..................... 558/46
5,144,042 A   9/1992   Seido et al. ................. 548/541
5,780,649 A   7/1998   Yuasa et al. ................. 549/313

FOREIGN PATENT DOCUMENTS

JP          2-174733        7/1990

OTHER PUBLICATIONS

Yuasa, Yoshifumi, et al., "Practical synthesis of (S)–4–hydroxytetrahydrofuran–2–ones, (S)–3–hydroxytetrahydrofuran, and their ( R )–enantiomers", Liebigs Ann./Recl., 1997(9), p. 1877–1879.

*Primary Examiner*—Bernard Dentz
(74) *Attorney, Agent, or Firm*—Sughrue Mion, PLLC

(57) ABSTRACT

An industrial advantage process for producing high-purity 3-hydroxytetrahydrofuran easily and simply, which comprises reducing a 4-halo-3-hydroxybutyric acid ester (1) with a boron hydride compound and/or an aluminum hydride compound as a reducing agent in an organic solvent immiscible with water;

treating the reaction mixture with an acid and water to thereby effect conversion to the corresponding 4-halo-1,3-butanediol and at the same time giving an aqueous solution containing said compound;

carrying out the cyclization reaction of the 4-halo-1,3-butanediol in said aqueous solution;

extracting the resulting 3-hydroxytetrahydrofuran from the 3-hydroxytetrahydrofuran-containing aqueous solution using an organic solvent immiscible with water; and isolating the 3-hydroxytetrahydrofuran by concentration and/or distillation of the solution obtained.

67 Claims, No Drawings

PROCESS FOR THE PREPARATION OF 3-HYDROXYTETRAHYDROFURAN

This application is a 371 of PCT/JP00/02431 filed Apr. 14, 2000.

TECHNICAL FIELD

The present invention relates to a process for producing a 3-hydroxytetrahydrofuran, particularly an optically active 3-(S)-hydroxytetrahydrofuran of high quality, in a simple, easy and industrially advantageous manner and in high yield.

BACKGROUND ART

3-Hydroxytetrahydrofuran is a compound of great value as a synthetic intermediate of medicinals and agrochemicals. The known technology for the production thereof comprises reducing a 4-halo-3-hydroxybutyric acid ester, which is readily available, and cyclizing the resulting 4-halo-1,3-butanediol. Specifically, production processes of 3-hydroxytetrahydrofuran are known which comprise reducing a 4-halo-3-hydroxybutyric acid ester with sodium borohydride in an organic solvent miscible with water, such as tetrahydrofuran (hereinafter referred to as THF), and cyclizing the resulting 4-halo-1,3-butanediol in aqueous hydrochloric acid to give 3-hydroxytetrahydrofuran [e.g. Japanese Kokai Publication Hei-09-77759; Liebigs Ann./Recl., page 1877 (1997)].

The steps involved in a typical production process among these as described are as follows:

Step 1: Reducing ethyl 4-chloro-3-hydroxybutyrate with sodium borohydride in THF;

Step 2: Adding aqueous hydrochloric acid to the concentration residue of the reaction mixture, extracting the mixture with ethyl acetate, dehydrating the extract with a solid desiccant, separating the desiccant by filtration and removing the extractant solvent by concentration, to give 4-chloro-1,3-butanediol as an oil;

Step 3: Dissolving this oil in aqueous hydrochloric acid and heating the solution to cause cyclization;

Step 4: Neutralizing the reaction mixture, removing water by concentration, adding methanol to the residue and removing the precipitated inorganic salt by filtration; and Step 5: Concentrating and distilling the filtrate to recover 3-hydroxytetrahydrofuran.

However, such a process requires complicated procedural steps such as a plurality of concentration and solid-liquid separation procedures. If a concentration procedure is omitted and water is directly added to the reaction mixture, a mixed solvent composed of the solvent and water will be formed, since the solvent is miscible with water. Investigations made by the present inventors revealed that if the cyclization reaction is then carried out in such a solvent, unfavorable results are inevitable, for example the rate of reaction decreases and the impurity content increases. Therefore, in carrying out the reduction reaction using a organic solvent miscible with water, it is essential to interpose a step of removing this organic solvent prior to addition of water to the reaction mixture. The prior art processes are thus low in productivity and cannot be said to be fully suited for commercial production.

Furthermore, in the prior art processes, generally the yield in the reduction step is 86% and the yield in the cyclization step is 68 to 79%, hence the yield of the desired product is 58 to 68%. These figures are not necessarily satisfactory. The prior art processes have further problems with respect to the quality of the desired product; it is known that, in the reduction reaction, 3,4-epoxy-1-butanol is formed as a byproduct (the byproduct yield being about 16 to 21%; Japanese Kokai Publication Hei-02-174733) and, in the cyclization reaction, 2,5-dihydrofuran is formed as a byproduct [the byproduct yield being about 15%; Liebigs Ann./Recl., page 1877 (1997)].

As mentioned above, in the state of art, no simple, easy and efficient processes are known, to say nothing of processes that may be carried out on a commercial scale with advantage, for producing high-quality 3-hydroxytetrahydrofuran in high yield by reduction of a 4-halo-3-hydroxybutyric acid ester and cyclization of the resulting 4-halo-1,3-butanediol.

In view of the above state of the art, it is an object of the present invention to provide a simple, easy and industrially advantageous process for producing high-quality 3-hydroxytetrahydrofuran (3) by reducing a 4-halo-3-hydroxybutyric acid ester (1) and cyclizing the resulting 4-halo-1,3-butanediol (2).

DISCLOSURE OF THE INVENTION

The present invention provides a process for producing a 3-hydroxytetrahydrofuran of the general formula (3):

(3)

by reducing a 4-halo-3-hydroxybutyric acid ester of the general formula (1):

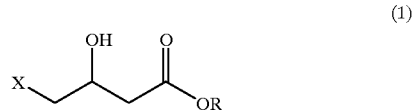

(1)

wherein R represents an ester-forming protective group and X represents a halogen atom and cyclizing the resulting 4-halo-1,3-butanediol of the general formula (2):

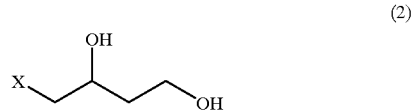

(2)

wherein X represents a halogen atom which comprises:

Step 1: Reducing a 4-halo-3-hydroxybutyric acid ester (1) with a boron hydride compound and/or an aluminum hydride compound as a reducing agent in an organic solvent immiscible with water;

Step 2: Treating the obtained reaction mixture with an acid and water to thereby effect conversion to the corresponding 4-halo-1,3-butanediol (2) and at the same time giving an aqueous solution containing said compound;

Step 3: Carrying out the cyclization reaction of the 4-halo-1,3-butanediol (2) in said aqueous solution;

Step 4: Extracting the resulting 3-hydroxytetrahydrofuran (3) from the obtained aqueous solution containing 3-hydroxytetrahydrofuran with an organic solvent immiscible with water; and Step 5: Isolating the 3-hydroxytetrahydrofuran (3) by concentration and/or distillation of the solution obtained.

The present invention also provides a process for producing a 4-halo-1,3-butanediol which comprises reducing a 4-halo-3-hydroxybutyric acid ester (1) with a boron hydride compound and/or an aluminum hydride compound as a reducing agent in an organic solvent immiscible with water and treating the obtained reaction mixture with an acid and water to thereby effect conversion to the corresponding 4-halo-1, 3-butanediol (2) and at the same time giving an aqueous solution containing said compound.

The present invention further provides a process for producing a 3-hydroxytetrahydrofuran (3) by cyclizing a 4-halo-1,3-butanediol (2) in an aqueous solution which comprises carrying out the cyclization reaction under weakly acidic to neutral conditions.

The present invention further provides a process for recovering a 3-hydroxytetrahydrofuran which comprises extracting 3-hydroxytetrahdyrofuran from an aqueous solution containing 3-hydroxytetrahydrofuran with an organic solvent immiscible with water at a temperature not lower than 40° C.

The present invention further provides a process for recovering a 3-hydroxytetrahydrofuran which comprises extracting 3-hydroxytetrahydrofuran from an aqueous solution containing 3-hydroxytetrahydrofuran with a monohydric alcohol containing 4 to 8 carbon atoms.

The present invention further provides a process for recovering a 3-hydroxytetrahydrofuran from a mixture comprising 3-hydroxytetrahydrofuran and a boron compound and/or an aluminum compound by distillation which comprises treating the mixture comprising 3-hydroxytetrahydrofuran and a boron compound and/or an aluminum compound with a monohydric alcohol containing 1 to 3 carbon atoms or a polyhydric alcohol containing at least 6 carbon atoms in carrying out the distillation.

Lastly, the present invention provides a process for recovering a 3-hydroxytetrahydrofuran which comprises carrying out distillation (inclusive of rectification) of 3-hydroxytetrahydrofuran in the presence of a base.

In the following, the present invention is described in detail.

The five-step process for producing a 3-hydroxytetrahydrofuran is described below in detail. The processes according to other aspects of the present invention can also be carried out by the same techniques mentioned hereinbelow.

In the first step of this production process, a 4-halo-3-hydroxybutyric acid ester represented by the above general formula (1) [hereinafter referred to also as "4-halo-3-hydroxybutyric acid ester (1)"] is reduced with a boron hydride compound and/or an aluminum hydride compound in an organic solvent immiscible with water to cause formation of the corresponding 4-halo-1,3-butanediol represented by the above general formula (2) [hereinafter referred to also as "4-halo-1,3-butanediol (2)"].

The symbol R in the above general formula (1) represents an ester-forming protective group. The term "ester-forming protective group" as used herein means a group capable of protecting a carboxylic acid by forming an ester therewith. The ester-forming protective group is not particularly restricted. Thus, it may be a conventional ester-forming protective group, preferably an alkyl group, more preferably an alkyl group containing 1 to 4 carbon atoms, most preferably an ethyl group.

The symbol X in the above general formulas (1) and (2) represents a halogen atom, which is a leaving atom capable of leaving under formation of an ether bond between the hydroxy group at position 1 and the carbon atom at position 4 in the general formula (2). It is preferably chlorine, bromine or iodine, more preferably chlorine.

The reaction substrate, namely 4-halo-3-hydroxybutyric acid ester (1) is generally prepared by reducing a 4-haloacetoacetic acid ester, which is readily available. For obtaining an optically active form of (1), which is useful as a raw material for the synthesis in the pharmaceutical and agrochemical field, in particular, methods are known which use a chemical agent capable of asymmetric reduction, or a microorganism or an enzyme. Thus, said form can be prepared by the methods described in Japanese Kokai Publication Hei-01-211551, J. Am. Chem. Soc., vol. 105, p. 5925 (1983) and Japanese Kokoku Publication Hei-04-7195, for instance. In the production process according to the present invention, this compound, when it is optically active, can give the 4-halo-1,3-butanediol (2) and 3-hydroxytetrahydrofuran (3) while the optical activity is retained. When, for example, the process of the present invention is carried out using a 4-halo-3-(S)-hydroxybutyric acid ester, 3-(S)-hydroxytetrahydrofuran can be obtained with high purity and in high yield.

The reducing agent to be used is a boron hydride compound and/or an aluminum hydride compound. More specifically, the reducing agent includes but is not limited to alkali metal borohydrides, alkaline earth metal borohydrides, alkali metal aluminum hydrides, dialkylaluminum hydrides and diborane, among others. These may be used singly or two or more of them may be used in a suitable combination. The salt-forming alkali metal in the reducing agent is, for example, lithium, sodium or potassium and the alkaline earth metal is calcium or magnesium. In consideration of the ease of handling and from other viewpoints, alkali metal borohydrides are preferred, and sodium borohydride is particularly preferred. Together with such a reducing agent, an activator generally known in the art may be combinedly used for improving the reducing power of the reducing agent.

The amount of the reducing agent is not particularly restricted but is preferably such that hydrogen is provided in an amount not less than the stoichiometric amount relative to the 4-halo-3-hydroxybutyric acid ester (1). For example, the reduction can be effected using sodium borohydride in an amount of not less than 0.5 mole, preferably not less than 0.75 mole, per mole of the 4-halo-3-hydroxybutyric acid ester (1). From the economic viewpoint, said amount is preferably not more than 10.0 moles, more preferably not more than 5.0 moles, still more preferably not more than 2.0 moles.

The concentration of the 4-halo-3-hydroxybutyric acid ester (1) in the reaction mixture cannot be specifically defined since it may vary according to the kind of the reaction solvent employed. Generally, however, it may, for example, be 1 to 50% by weight, preferably 5 to 40% by weight, more preferably 10 to 30% by weight.

The reaction temperature cannot be specifically defined since it depends on the reducing agent and reaction solvent employed. Generally, however, it is within the range between the solidifying point and the boiling point of the reaction solvent employed, preferably 20 to 80° C. For causing the reaction to proceed efficiently and, in particular, for driving the reaction to completion in a period of time suited for a commercial scale production, a temperature of not lower than 40° C. is preferred. On the other hand, for suppressing side reactions or decomposition, it is important that the reaction temperature is not excessively high. For example, it is preferred that the reaction is carried out at a temperature not higher than 80° C., preferably not higher than 60° C. The reaction time is generally about 24 hours at longest.

The reduction reaction according to the invention is an exothermic reaction and is accompanied with rapid heat generation particularly in the initial stage thereof. It is, therefore, important to adequately control the reaction so that it may proceed smoothly. From this point of view, the reaction is preferably carried out by adding the 4-halo-3-hydroxybutyric acid ester (1) and/or the above reducing agent in a continuous manner or intermittently in portions. Specifically, the reaction may be carried out while adding either of the 4-halo-3-hdyroxybutyric acid ester (1) or the reducing agent or while adding both compounds simultaneously. For carrying out the reduction reaction in a simple and safe manner on a commercial scale, it is generally preferred that the reducing agent is gradually added to the solution of the 4-halo-3-hydroxybutyric acid ester (1). The duration of this addition is preferably not less than 1 hour, more preferably not less than 2 hours, still more preferably not less than 5 hours.

The organic solvent to be used as the solvent in this reduction reaction, which is immiscible with water, is generally an organic solvent having a physical property such that when it is gently stirred together with an equal volume of pure water under a pressure of one atmosphere and at a temperature of 20° C., the resulting mixture, after stopping of the flow, shows a heterogeneous appearance. The solubility in water is not particularly restricted but an organic solvent having a solubility in water of not more than 30% by weight, in particular not more than 10% by weight, is generally preferred, and an organic solvent having a solubility in water of not more than 5% by weight, in particular not more than 1% by weight, is more preferred.

The above organic solvent immiscible with water preferably has a boiling point not lower than 40° C., more preferably not lower than 50° C. When a solvent having a boiling point lower than 40° C. is used, the reduction reaction temperature cannot be raised, so that the reaction time may be prolonged or the rapid heat generation due to the reduction reaction may readily result in bumping, among other troubles, making it difficult to duly control the reaction. These and other problems handicap the process in productivity and safety, which are especially important in commercial-scale production.

As concrete examples of the organic solvent immiscible with water which are preferred from the above point of view, there may be mentioned, among others, aromatic hydrocarbons such as benzene, toluene, xylene and ethylbenzene; acetic acid esters such as methyl acetate, ethyl acetate, n-propyl acetate, isopropyl acetate, n-butyl acetate, isobutyl acetate and tert-butyl acetate; aliphatic hydrocarbons such as hexane, cyclohexane and methylcyclohexane; halogenated hydrocarbons such as methylene chloride and chloroform; and ethers such as diisopropyl ether, methyl tert-butyl ether and ethylene glycol dibutyl ether. Among them, hydrocarbons (in particular aromatic hydrocarbons) and acetic acid esters are preferred, and toluene and acetic acid $C_1$–$C_4$ alkyl esters are more preferred. These organic solvents may be used singly or two or more of them may be used combinedly. Aprotic organic solvents immiscible with water are also preferred as the organic solvent immiscible with water.

When the reduction reaction is carried out using the above solvent, the formation of those impurities which are known in the art, such as 3,4-epoxy-1-butanol (Japanese Kokai Publication Hei-02-174733), can be prevented and the 4-halo-1,3-butanediol (2) can be produced in high yields.

In the second step of the production process according to the present invention, the reaction mixture obtained in step 1 is treated using an acid and water to thereby cause formation of the 4-halo-1,3-butanediol (2) and causing the same to transfer to the aqueous phase; an aqueous solution containing the same is thus obtained.

The acid to be used in this step is not particularly restricted but, from the practicality viewpoint, inorganic acids, in particular hydrochloric acid and sulfuric acid, are preferred. These may be used singly or two or more of them may be used combinedly. An aqueous solution obtained by diluting concentrated hydrochloric acid or concentrated sulfuric acid with water may be used as the acid and water.

The acid is used in an amount sufficient to neutralize the basic component resulting from the reducing agent used in step 1 and convert the same to an inorganic salt, that is to say generally in an at least equimolar amount relative to the reducing agent. The reaction mixture is preferably rendered neutral to acidic by using the acid in an amount at least equimolar to the reducing agent.

The amount of water is preferably such that the 4-halo-1,3-butanediol (2) produced can transfer to the aqueous phase to a satisfactory extent.

The treatment of the reaction mixture obtained in step 1 with an acid and water is carried out generally by admixing the reaction mixture simultaneously with the acid and water. It is also possible to first mix the reaction mixture with the acid and then mix the resulting mixture with water. The method of such mixing is not particularly restricted. Thus, the acid can be added to the reaction mixture or preferably the reaction mixture is added to the acid. Such procedure is preferably carried out at a low temperature, preferably at a temperature between room temperature and the freezing point of the solvent.

Since, in the process according to the invention, an organic solvent immiscible with water is used in step 1, the addition of the acid and water to the reaction mixture results in separation into two phases, of which the aqueous phase as it is can be used in step 3. By removing the organic phase by liquid-liquid separation, the aqueous solution containing the 4-halo-1,3-butanediol (2) can be obtained with ease. Further, it is also possible to extract the organic layer separated with water to thereby further increase the yield.

For increasing the yield, the separation of the organic phase by liquid-liquid separation is preferably carried out at a low temperature. By doing so, the transfer of the 4-halo-1,3-butanediol (2) to the organic phase can be prevented and the yield can be prevented from decreasing. More specifically, the operation temperature is preferably within the range between 30° C. and the freezing point of the solvent, more preferably at a temperature not higher than 20° C., still more preferably not higher than 10° C.

To separate and remove the organic phase in that manner is preferred also from the viewpoint of further reducing the amount of trace impurities and byproducts occurring in the reaction mixture obtained in step 1. It is also possible, however, to collect the aqueous solution by concentrating the organic layer to thereby remove the organic solvent. In the aqueous solution obtained in this step, there may coexist the organic phase in an amount of the range not adversely affecting the cyclization reaction in step 3 and, in that case, the organic phase and aqueous phase may form a binary system.

Then, in step 3, the cyclization reaction of the 4-halo-1, 3-butanediol (2) is effected in the aqueous solution obtained instep 2. Although the boron compound and/or aluminum compound resulting from decomposition of the reducing agent used in step 1 and another inorganic salt or the like coexist in the aqueous solution obtained in step 2, this cyclization reaction can give 3-hydroxytetrahydrofuran (3) in a high yield.

Even when the cyclization reaction is carried out in the two-phase system in which the organic solvent immiscible with water coexists, namely without removing that organic solvent immiscible with water in step 2, the cyclization reaction can proceed smoothly and give 3-hydroxytetrahydrofuran (3) in a high yield. This reaction mode is also effective in transferring impurities to the organic phase to thereby reduce the impurity concentration in the aqueous phase in which the cyclization reaction proceeds substantially predominantly, hence to thereby prevent side reactions and reduce the amount of byproduct impurities. Furthermore, that reaction mode is advantageous in that since the distribution coefficient of the cyclization product 3-hydroxytetrahydrofuran (3) in the organic solvent immiscible with water is generally lower as compared with the precyclization compound 4-halo-1,3-butanediol (2), a higher yield can be obtained at a small loss of the desired product into the organic phase even when the removal of the organic phase is carried out after the cyclization reaction as compared with before the cyclization reaction.

The operation temperature during the cyclization reaction is not particularly restricted. While the cyclization reaction can proceed even at around room temperature, it is preferred that the reaction is carried out with heating at a temperature not lower than room temperature so that the rate of reaction may be increased and the reaction may be driven to completion in a shorter time. Thus, it is preferably carried out at not lower than 40° C., more preferably at not lower than 50° C., still more preferably at not lower than 70° C. Generally, it is advantageous to carry out the reaction by raising the temperature to the vicinity of the boiling point of the reaction system.

This cyclization reaction is preferably carried out under acidic to neutral conditions. Although the cyclization reaction can proceed under basic conditions as well, basic conditions are generally unfavorable because of a tendency toward formation of impurities. Generally, therefore, the reaction is preferably started under neutral to acidic conditions. However, the reaction mixture is gradually acidified by the acid component (e.g. hydrogen halide) formed with the progress of the cyclization reaction. Since an excessively strong acidity may readily cause impurity formation, it is preferred that the cyclizareaction reaction is started under neutral conditions, for instance, so that the adverse effects of the acid component may be minimized. In this way, the formation of 2,5-dihydrofuran as a byproduct, which is readily formed when the cyclization reaction is started under strongly acidic conditions, as known in the art [Liebigs Ann./Recl., p. 1877 (1997)], can be suppressed and a higher yield of 3-hydroxytetrahydrofuran can be obtained.

Still more preferably, from the viewpoint of minimizing the adverse effects of the acid in the cyclization reaction, the cyclization reaction is carried out under weakly acidic to neutral conditions while maintaining an appropriate acidity by neutralizing, with a base, the acid component (e.g. hydrogen halide) formed with the progress of the reaction, whereby 3-hydroxytetrahydrofuran (3) can be produced with the highest yield and quality. The appropriate acidity in that case varies according to the operation temperature and concentration in the cyclization reaction, the coexisting inorganic salt and other species and amounts thereof, hence can never be specifically defined. Preferably, however, the reaction is carried out while neutralizing the acid component to a pH range of 2 to 7, more preferably 2 to 6.

The base to be used for neutralizing the above acid component is not particularly restricted but includes, among others, inorganic bases such as alkali metal or alkaline earth metal hydroxides, carbonates and hydrogen carbonates; and organic bases such as secondary amines, tertiary amines and quaternary ammonium hydroxides. More specifically, it includes but is not limited to alkali metal hydroxides such as sodium hydroxide, potassium hydroxide and lithium hydroxide; alkali metal carbonates such as sodium carbonate, potassium carbonate and lithium carbonate; alkali metal hydrogen carbonates such as sodium hydrogen carbonate and potassium hydrogen carbonate; alkaline earth metal hydroxides such as magnesium hydroxide and calcium hydroxide; alkaline earth metal carbonates such as calcium carbonate and barium carbonate; secondary amines such as dimethylamine, diethylamine, diisopropylamine and dicyclohexylamine; tertiary amines such as triethylamine, tripropylamine, tributylamine, triamylamine, pyridine and N-methylmorpholine; and quaternary ammonium hydroxides such as tetramethyl-, tetraethyl-, tetrapropyl-, tetrabutyl-, tetraamyl-, tetrahexyl- and benzyltrimethylammonium hydroxides. Preferred, among these bases, from the viewpoints of inexpensiveness, ease of handling and ease of waste water treatment, among others, are inorganic bases, in particular alkali metal hydroxides such as sodium hydroxide, potassium hydroxide and lithium hydroxide, in particular sodium hydroxide and potassium hydroxide.

From the operability viewpoint, the above inorganic base is preferably used in the form of an aqueous solution. For example, an aqueous solution of an alkali metal hydroxide having a concentration of 2 to 20 N, preferably 5 to 20 N, is used with advantage. The base species mentioned above may be used singly or two or more of them may be used combinedly. The reaction may be carried out while adding these bases gradually at a rate such that the reaction mixture may be maintained at an appropriate pH. It is also possible to add sodium carbonate, barium carbonate, calcium carbonate or disodium hydrogen phosphate to thereby utilize the pH buffer action thereof.

The concentration of the 4-halo-1,3-butanediol (2) in the aqueous solution in carrying out the cyclization reaction is not restricted. An excessively high concentration, however, is not preferred since the rate of reaction decreases. Generally, it is 1 to 50% by weight, preferablyl to 35% by weight, more preferably 1 to 20% by weight. By carrying out the cyclization reaction while maintaining the acidity at a proper level, as mentioned above, it is possible to increase the reaction concentration and carry out the cyclization reaction favorably at a concentration of 1 to 30% by weight, preferably 5 to 30% by weight.

In cases that 3-hydroxytetrahydrofuran (3) is used in such fields where it is desirable the slight impurity content, which is already slight, is reduced still further for the production of products of higher quality, for example medicinals, it is also preferred that the aqueous solution obtained in step 3 is washed with an organic solvent immiscible with water. This is effective in further reducing the slight impurity content in the aqueous phase and thus improving the quality of the product 3-hydroxytetrahydrofuran (3).

When the cyclization reaction is carried out in a two-phase system in which water and an organic solvent immiscible with water coexist, mere recovery of the aqueous solution containing 3-hydroxytetrahydrofuran (3) after the cyclization reaction by removal of the organic phase by liquid-liquid separation can result in reduction of impurities from the aqueous phase, hence in quality improvement.

These procedures (washing and organic phase removal by liquid-liquid separation) are preferably carried out at low temperatures. By this, the distribution ratio of 3-hydroxytetrahydrofuran (3) in the organic layer, hence the loss thereof in the organic phase, can be reduced and the yield can be increased accordingly. Specifically, the procedures are preferably carried out at an operation temperature lowered to 30° C. or below, more preferably to 20° C. or below, still more preferably to a level of 10° C. or below down to the freezing point of the solvent.

In step 4, 3-hydroxytetrahydrofuran (3) is extracted from the aqueous solution containing 3-hydroxytetrahydrofuran (3) obtained in step 3, using an organic solvent immiscible with water. By this extraction procedure, the inorganic salt(s) and reducing agent-derived boron compound or aluminum compound, which coexist in the aqueous solution, can be separated from the desired product to give an organic solution containing 3-hydroxytetrahydrofuran (3).

The organic solvent immiscible with water to be used here is not particularly restricted. For example, it maybe selected from among those organic solvents immiscible with water which can be used in the reduction reaction mentioned above. In addition to them, monohydric alcohols containing 4 to 8 carbon atoms, for example butanols such as 1-butanol, 2-butanol and isobutanol, can be used. Preferred are aromatic hydrocarbons, acetic acid esters and monohydric alcohols containing 4 to 8 carbon atoms. More preferred are acetic acid esters, in particular acetic acid $C_1$–$C_4$ alkyl esters, most preferably ethyl acetate. These organic solvents may be used singly or two or more of them may be used combinedly.

Generally, the aqueous solution obtained in step 3 is in an acidified state. It may be subjected to extraction either as it is under acid conditions or after neutralization with a base. It is generally preferred that the extraction procedure is carried out under neutral conditions. The base to be used for the neutralization is not particularly restricted but includes, among others, alkali metal hydroxides such as sodium hydroxide and potassium hydroxide; alkaline earth metal hydroxides such as calcium hydroxide and magnesium hydroxide; alkali metal hydrogen carbonates such as sodium hydrogen carbonate and potassium hydrogen carbonate; alkali metal carbonates such as sodium carbonate and potassium carbonate; alkaline earth metal carbonates such as magnesium carbonate and calcium carbonate; and so forth. Aqueous ammonia and organic bases such as triethylamine, pyridine and other amines may also be used. These bases may be used singly or two or more of them may be used combinedly.

It is also preferred that the aqueous solution obtained in step 3 is once basified with a base, then neutralized with an acid and subjected to extraction. By such treatments, the impurities contained in the solution are converted to impurities readily transferring to the aqueous phase and, which remain in the aqueous phase on the occasion of extraction following neutralization, the purity of the desired product extracted can be increased. This basification can be carried out using one of the bases mentioned above. For attaining increased treatment effects, the pH is preferably adjusted to not less than 10, more preferably not less than 12, though such level is not absolutely necessary. These procedures can be performed at a temperature not lower than the freezing point of the solvent and the time required therefor can be shortened by raising the temperature within the range from room temperature to the boiling point of the solvent. The treatment time depends on the pH and temperature but generally is about 0.1 to 24 hours. After treatment with a base, the aqueous phase is preferably subjected to extraction after neutralization.

The extraction operation temperature in step 4 cannot be specifically defined since it varies depending on the organic solvent employed but the extraction can be effected within the range of the solidifying point to the boiling point of the solvent employed, generally at 20 to 100° C. High temperature extraction is particularly preferred, however. Thus, the extraction procedure is performed preferably at 40° C. or above, more preferably at 50° C. or above, most preferably at 60° C. or above. Particularly when a hydrocarbon or acetic acid ester or the like is used as the solvent, high temperature extraction is preferred for increasing the extraction efficiency.

By using such a monohydric alcohol containing 4 to 8 carbon atoms as mentioned above as the solvent, a high extraction effect can be produced even at around room temperature. It is also possible, however, to carry out the extraction at an elevated liquid temperature to further increase the extracting effect. Specifically, it is also possible to carry out the extraction using a monohydric alcohol containing 4 to 8 carbon atoms at a temperature of 40° C. or above.

In step 5, the extract solution obtained in step 4 is concentrated and/or distilled to isolate 3-hydroxytetrahydrofuran (3). Thus, the extract is concentrated to thereby remove the organic solvent or the extract is subjected to distillation (inclusive of rectification), to thereby isolate 3-hydroxytetrahydrofuran (3). It is also possible to concentrate the extract to thereby remove the solvent and then further distill (or rectify) the concentrate to thereby isolate 3-hydroxytetrahydrofuran (3). In this case, the residue after concentration as it is can be heated under reduced pressure to effect distillation.

In purifying and isolating 3-hydroxytetrahydrofuran (3) by distillation (inclusive of rectification), the reducing agent-derived boron and/or aluminum compounds occurring in slight amounts in the extract obtained in step 4 may lower the distillation yield. Therefore, for maximizing the final distillation yield, it is preferred that, in carrying out the distillation in step 5, the solution and/or concentrate containing 3-hydroxytetrahydrofuran (3) is treated with an alcohol to thereby remove those impurities in advance. By adding a monohydric alcohol containing 1 to 3 carbon atoms, such as methanol and ethanol, for instance, it is possible to form compounds lower in boiling point than 3-hydroxytetrahydrofuran (3) and distill off these previously. On the other hand, by adding a polyhydric alcohol containing not less than 6 carbon atoms, such as polyethylene glycol and sorbitol, it is possible to cause compounds higher in boiling point than 3-hydroxytetrahydrofuran (3) to remain. This step can be used with advantage for purifying and isolating 3-hydroxytetrahydrofuran by distillation when this has been contaminated with the boron compound and/or aluminum compound mentioned above.

The amount of use of such alcohol should vary with the kind of alcohol and the kinds and amounts of contaminants derived from the reducing agent and cannot be defined in general terms. Generally, however, the alcohol is used in at least an equimolar amount relative to the amount of said contaminants derived from the reducing agent. For an improved treatment effect, it is rather preferred to use the alcohol in excess taking the influence of the water concomitantly present into consideration, particularly when a monohydric alcohol containing 1 to 3 carbon atoms is used. Specifically, a monohydric alcohol containing 1 to 3 carbon atoms, for instance, is used in an amount of not less than 50% by weight, preferably not less than the same weight %, based on the weight of 3-hydroxytetrahydrofuran (3). A polyhydric alcohol containing not less than 6 carbon atoms is used for the above treatment in an amount of not less than 20% by weight, more preferably not less than 30% by weight. In the above manner, the coexisting boron compounds and/or aluminum compounds can be effectively removed. It is preferred that the residual amount of boron compounds and/or aluminum compounds after the treatment be not more than 10 mole percent, more preferably not more than 5 mole percent, per mole of 3-hydroxytetrahydrofuran. Then, the distillation can favorably be conducted and the distillation yield can be maximized.

In cases that 3-hydroxytetrahydrofuran (3) is purified by distillation (inclusive of rectification) on an industrial scale, a prolonged heating operation is required and, therefore, the related impurities contained in slight amounts, such as the 4-halo-3-hydroxybutyric acid ester (1) and/or 4-halo-1,3-butanediol (2) and their related compounds, may gradually undergo thermal decomposition and the resulting decomposition products may find their way into the desired product fraction during distillation, tending to cause problems such as quality deterioration. It was found that, upon these thermal decompositions, acid components are released and acidification progresses accordingly, leading to a tendency toward promoted thermal decomposition. From this point of view, it is also preferred to use an apparatus in which the heat hysteresis can be reduced and the distillation can be carried out while suppressing the thermal decomposition, for example a wiped film evaporator.

However, when the distillation is carried out using an ordinary distillation column in common use, it is good practice to treat the solution containing 3-hydroxytetrahydrofuran (3) and/or a concentrate thereof with an acid, for instance, preferably to add an acid followed by heating before distillation to promote thermal decomposition. This practice inhibits the formation of impurities in the course of distillation to thereby contribute to an improved purification effect of the distillation in a stable manner. It is preferred that a solvent is used in this acid treatment. Thus, it is also preferred to carry out the acid treatment in solution in a monohydric alcohol containing 1 to 3 carbon atoms prior to the distillation step.

The acid to be added is not particularly restricted but may be an inorganic acid or an organic acid. From the practicality viewpoint, inorganic acids, in particular hydrochloric acid and sulfuric acid, are preferred. These may be used singly or two or more of them may be used combinedly. The addition amount of the acid is not particularly restricted but is preferably not less than 0.1% by weight, more preferably not less than 0.2% by weight, still more preferably not less than 0.5% by weight, relative to 3-hydroxytetrahydrofuran (3). The operation temperature in heating treatment following addition of an acid is not particularly restricted but is, for example, room temperature up to the boiling point of the system employed. The time of acid treatment is generally not less than 0.1 hour, preferably not less than 0.5 hour.

The distillation (inclusive of rectification) of 3-hydroxytetrahydrofuran (3) for purification is also preferably carried out in the presence of a base. This is effective in neutralizing the acid components released upon thermal decomposition of such coexisting impurities as mentioned above and increasing the distillation/purification effect while suppressing the influences of the acid components. Furthermore, it contributes significantly to an increased heat stability of 3-hydroxytetrahydrofuran (3). By conducting the distillation mentioned above (inclusive of rectification) for purification, the quality and yield of the desired product can be increased.

The base to be used in that case is not particularly restricted but preferably is a base higher in boiling point than 3-hydroxytetrahydrofuran (3), more preferably an inorganic base. Specifically, there may be mentioned alkali metal hydroxides such as sodium hydroxide and potassium hydroxide; alkaline earth metal hydroxides such as calcium hydroxide and magnesium hydroxide; alkali metal hydrogen carbonates such as sodium hydrogen carbonate and potassium hydrogen carbonate; alkali metal carbonates such as sodium carbonate and potassium carbonate; alkaline earth metal carbonates such as magnesium carbonate and calcium carbonate; and so on. Alkali metal hydrogen carbonates and alkali metal carbonates are preferred, alkali metal hydrogen carbonates, in particular sodium hydrogen carbonate, are preferred. These may be used singly or two or more maybe used combinedly. The addition amount of these bases is not particularly restricted. Generally, the bases are used in an amount of 0.1 to 30% by weight based on the material to be distilled but, from the viewpoint of economy and/or operability, the use thereof in an amount of not more than 10% by weight is preferred, more preferably not more than 5% by weight, still more preferably not more than 2% by weight.

A preferred embodiment of the present invention in which ethyl 4-chloro-3-(S)-hydroxybutyrate is used as the reaction substrate may be follows.

Ethyl 4-chloro-3-(S)-hydroxybutyrate is reduced with sodium borohydride in toluene, and the reaction mixture is mixed with aqueous hydrochloric acid to give an aqueous solution of 4-chloro-1,3-(S)-butanediol. This aqueous solution is heated as it is to thereby effect the cyclization reaction, preferably while adequately neutralizing the acid component resulting from the reaction, followed by extraction with ethyl acetate under warming, further followed by concentration and/or distillation, to give 3-(S)-hydroxytetrahydrofuran.

BEST MODES FOR CARRYING OUT THE INVENTION

The following examples illustrate the present invention in further detail. These examples, however, are by no means limitative of the scope of the present invention. Analyses were performed by liquid chromatography (column: ALLTIMA C8, 5 μm, φ4.6 mm×250 mm; column temperature: 30° C.; mobile phase; acetonitrile/distilled water [3/97]; detection; RI) and gas chromatography (column: PEG 20M 10% Chromosorb WAW, φ 3.2 mm×3.1 m; column temperature: 130° C.; detection: FID).

EXAMPLE 1

Sodium borohydride (104.1 g) was suspended in 2;300 mL of toluene, and 458.5 g of ethyl 4-chloro-3-(S)-hydroxybutyrate (optical purity: 99.4% ee) was added over 1 hour with stirring at 40° C. The reaction was then allowed to proceed for about 20 hours with continued stirring. After the reaction mixture was cooled to 10° C. or below, 286.7 g of concentrated hydrochloric acid and 940 ml of water were added, and the resultant mixture was stirred. The pH was adjusted to 7.0±0.2 by adding 88.6 g of a 30% aqueous solution of sodium hydroxide and, after the mixture was allowed to stand, the toluene phase was removed by liquid-liquid separation, whereby an aqueous phase containing 321.8 g (yield: 94%) of 4-chloro-1,3-(S)-butanediol was obtained.

This aqueous phase was heated to 74° C. In about 2 hours, the pH became 2 or below. Thereafter, the reaction was further allowed to proceed at 74 to 90° C. for 20 hours. After the mixture was cooled to 10° C. or below, the pH was adjusted to 7.0±0.2 by adding 327 g of a 30% aqueous solution of sodium hydroxide and the resulting mixture was heated to 70° C. Then, a continuous extraction and reduced-pressure concentration procedure was carried out at 70° C. using 2 liters of ethyl acetate. Methanol (460 g) was added to the residue obtained and, after concentration, the mixture was distilled under reduced pressure to give 198.8 g (yield: 87%; overall yield: 82%) of colorless 3-(S)-hydroxytetrahydrofuran. Purity: not less than 99%; optical purity: not less than 99%.

EXAMPLE 2

Sodium borohydride (22.0 g) was suspended in 528 mL of ethyl acetate, and 96.8 g of ethyl 4-chloro-3-hydroxybutyrate was added over 1 hour with stirring at 50 to 60° C. The reaction was then allowed to proceed for about 2 hours with continued stirring. The reaction mixture was then cooled to 10° C. or below and 60.5 g of concentrated hydrochloric acid and 100 ml of water were added, followed by vigorous stirring. The pH was adjusted to 7.0±0.2 using 26.1 g of a 30% aqueous solution of sodium hydroxide and, after the mixture was allowed to stand, the ethyl acetate phase was separated by liquid-liquid separation. The ethyl acetate phase was further extracted with 50 ml of water. As a result, an aqueous solution containing a total of 66.6 g (yield: 92%) of 4-chloro-1,3-butanediol was obtained.

EXAMPLE 3

A 192.5 g of an aqueous phase containing 38.5 g of 4-chloro-1,3-(S)-butanediol (concentration: 20.0% by weight) as obtained in Example 1 was heated to 70° C., whereupon the pH became 4 in about an hour. Thereafter, the reaction was allowed to proceed at 70 to 90° C. for 20 hours while maintaining the reaction mixture at pH 4 by gradually adding a 30% aqueous solution of sodium hydroxide. The reaction mixture obtained was cooled to 10° C. or below and adjusted to pH 7.0±0.2 using a 30% aqueous solution of sodium hydroxide, whereby 222.5 g of an aqueous solution was obtained. This aqueous solution contained 11.5% by weight (25.7 g, yield 95%) of 3-(S)-hydroxytetrahydrofuran.

EXAMPLE 4

The reaction was carried out in the same manner as in Example 3 while adjusting and maintaining the pH of the reaction mixture at the value specified in Table 1 and the yield of the resulting 3-(S)-hydroxytetrahydrofuran (3) and the percentage of the residual 4-chloro-1,3-butanediol (2) were determined to thereby investigate the influence of the pH on the cyclization reaction. The results are shown in Table 1.

TABLE 1

| Reaction condition pH | Yield of compound 3 (%) | Yield of compound 2 (%) |
| --- | --- | --- |
| <0 (unadjusted) | 85 | 5 |
| 1 | 87 | 4 |
| 3 | 94 | 1 |
| 4 | 95 | 1 |
| 6 | 93 | 1 |
| 5 | 91 | 1 |
| 8 | 67 | 1 |

EXAMPLE 5

Ethyl 4-chloro-3-(S)-hydroxybutyrate (144.7 g, optical purity: 99.4% ee) was dissolved in 720 mL of toluene, and 32.9 g of sodium borohydride was added over about 10 hours with stirring at 45° C. The reaction was further allowed to proceed for 5 hours with continued stirring. The reaction mixture was cooled to 20° C. or below and added to a mixture of 90.5 g of concentrated hydrochloric acid and 215 ml of water and cooled to 5° C. or below, and the resulting mixture was stirred. The pH was adjusted to 7.0±0.2 using a 30% aqueous solution of sodium hydroxide to give a water-toluene mixture containing 104.0 g (yield 96%) of 4-chloro-1,3-(S)-butanediol.

Upon heating to 85° C, the pH of this mixture solution fell to 4 in about an hour. Thereafter, the reaction was allowed to proceed at the same temperature for 20 hours while maintaining the pH of the reaction mixture at 4±0.5 by gradual dropwise addition of a 30% aqueous solution of sodium hydroxide. The residual amount of 4-chloro-1,3-(S)-butanediol became 0.8%. The mixture was cooled to 10° C. or below and adjusted to pH 7.0±0.2 using 100 g of a 30% aqueous solution of sodium hydroxide and then allowed to stand, and the toluene phase was removed by liquid-liquid separation. The aqueous phase obtained was heated to about 68° C. and continuously extracted with 1 L of ethyl acetate at 68° C. and the extract was concentrated under reduced pressure. To the residue was added 80 g of methanol, followed by concentration under reduced pressure. To the residue obtained were added 80 g of methanol and 0.8 g of concentrated hydrochloric acid, and the mixture was heated under reflux for about 2 hours. The mixture was concentrated under reduced pressure and, after addition of 1.2 g of sodium hydrogen carbonate, the residue was rectified under reduced pressure to give 60.9 g (yield 83%; overall yield 80%) of colorless 3-(S)-hydroxytetrahydrofuran. The purity of this product was not less than 99% and the optical purity was not less than 99%.

EXAMPLE 6

In the procedure of Example 1, an aqueous solution of 3-hydroxytetrahydrofuran was recovered after completion of the cyclization reaction. To 10 g of this aqueous solution was added 10 ml of the solvent mentioned in Table 2, and the mixture was stirred at the specified temperature for 10 minutes, allowed to stand for 10 minutes, and subjected to liquid-liquid separation, and the percentage of extraction was determined. In this manner, the relation between extraction temperature and percentage of extraction was examined. The results are shown in Table 2.

TABLE 2

| Extractant solvent | Extraction temperature (° C.) | Percentage of extraction (%) |
| --- | --- | --- |
| Ethyl acetate | 15 | 4 |
|  | 30 | 14 |
|  | 50 | 31 |
|  | 70 | 46 |
| 2-Butanol | 30 | 68 |

EXAMPLE 7

In the procedure of Example 1, the ethyl acetate extract containing 3-hydroxytetrahydrofuran was concentrated. To 10 g of the residue was added a specified amount of the alcohol indicated in Table 3, and the mixture was distilled to remove the methanol and the residual amount of boric acid was determined. The residue was further distilled and the percentage of recovery by distillation was determined. In this manner, the effects of the respective alcohols were investigated. The results are shown in Table 3. In the table, PEG 300 means a polyethylene glycol species having an average molecular weight of 300. The coexisting boric acid was assayed by the method comprising neutralization titration as a monobasic acid in the presence of sorbitol (Lectures in Experimental Chemistry, New Series, vol. 9, Analytical Chemistry I, published by Maruzen).

(Method) A sample, accurately weighed, was dissolved in 25 ml of distilled water and adjusted to pH 7. To this solution were added a few drops of the indicator phenolphthalein and about 5 g of sorbitol. The resulting solution was titrated with 0.1 N aqueous sodium hydroxide until the solution had assumed a pale red color, and the amount of boric acid was determined against a working curve constructed beforehand using predetermined amounts of boric acid.

TABLE 3

| Alcohol | Amount added (g) | Residual boric acid (mole %) | Percentage of recovery (%) |
| --- | --- | --- | --- |
| No addition | — | 16 | 85 |
| Sorbitol | 2 | — | 98 |
| Methanol | 5 | 10 | 93 |
| Methanol | 10 | 5 | 99 |
| PEG 300 | 3 | — | 99 |

The amount of residual boric acid is expressed in mole percent relative to 3-hydroxytetrahydrofuran.

EXAMPLE 8

A 10-g portion of the methanol concentrate containing 3-(S)-hydroxytetrahydrofuran as obtained in the procedure of Example 5 was heated to 120° C. with or without addition of 0.2 g of sodium hydrogen carbonate, and the percentage of residual 3-(S)-hydroxytetrahydrofuran was determined at timed intervals. In this manner, the effect of addition of the base was examined. The results are shown in Table 4.

TABLE 4

| $NaHCO_3$ | Percent residue (%) |
| --- | --- |
| No addition |  |
| 24 hours | 98 |
| 48 hours | 95 |
| Addition |  |
| 24 hours | 100 |
| 48 hours | 100 |

Industrial Applicability

The present invention, which has the above constitution, makes it possible to produce high purity 3-hydroxytetrahydrofuran in high yield and in a simple, easy and industrially advantageous manner starting with a 4-halo-3-hydroxybutyric acid ester, which is readily available, without resort to such complicated procedures as a plurality of concentration and solid-liquid separation procedures. It is also possible to produce 3-hydroxytetrahydrofuran having a high optical purity.

What is claimed is:

1. A process for producing a 3-hydroxytetrahydrofuran of the formula (3):

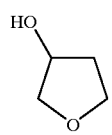

(3)

by reducing a 4-halo-3-hydroxybutyric acid ester of the general formula (1):

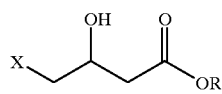

wherein R represents an ester-forming protective group and X represents a halogen atom
and cyclizing the resulting 4-halo-1,3-butanediol of the general formula (2):

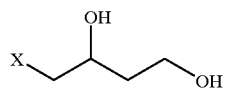

wherein X represents a halogen atom,
which comprises:
  Step 1: Reducing a 4-halo-3-hydroxybutyric acid ester (1) with a boron hydride compound and/or an aluminum hydride compound as a reducing agent in an organic solvent immiscible with water;
  Step 2: Treating the obtained reaction mixture with an acid and water to thereby effect conversion to the corresponding 4-halo-1,3-butanediol (2) and at the same time giving an aqueous solution containing said compound;
  Step 3: Carrying out the cyclization reaction of the 4-halo-1,3-butanediol (2) in said aqueous solution;
  Step 4: Extracting the 3-hydroxytetrahydrofuran (3) from the obtained aqueous solution containing 3-hydroxytetrahydrofuran with an organic solvent immiscible with water; and
  Step 5: Isolating the 3-hydroxytetrahydrofuran (3) by concentration and/or distillation of the solution obtained.

2. The process according to claim 1, wherein R in the general formula (1) is an alkyl group containing 1 to 4 carbon atoms.

3. The process according to claim 1, wherein X in the general formulas (1) and (2) is chlorine, bromine or iodine.

4. The process according to claim 1, wherein the organic solvent immiscible with water as used in step 1 is a hydrocarbon or an acetic acid ester.

5. The process according to claim 4, wherein the organic solvent immiscible with water as used in step 1 is toluene or an acetic acid $C_1$–$C_4$ alkyl ester.

6. The process according to claim 1, wherein the reduction reaction in step 1 is carried out at a temperature of 20 to 80° C.

7. The process according to claim 1, wherein the reduction reaction in step 1 is carried out by adding the reducing agent gradually to a solution of the 4-halo-3-hydroxybutyric acid ester (1).

8. The process according to claim 1, wherein the reducing agent is an alkali metal borohydride.

9. The process according to claim 8, wherein the alkali metal borohydride is sodium borohydride.

10. The process according to claim 1, wherein the acid used in step 2 is an inorganic acid.

11. The process according to claim 10, wherein the inorganic acid is hydrochloric acid or sulfuric acid.

12. The process according to claim 1, wherein, the reaction mixture is made acidic to neutral by treatment in step 2, with an acid and water.

13. The process according to claim 1, wherein the cyclization reaction in step 3 is carried out at a temperature not lower than 40° C.

14. The process according to claim 1, wherein the cyclization reaction in step 3 is carried out under acidic to neutral conditions.

15. The process according to claim 1, wherein the cyclization reaction in step 3 is started under neutral conditions.

16. The process according to claim 1, wherein the cyclization reaction in step 3 is carried out while maintaining the pH at 2 to 7 by neutralizing the acid component generated.

17. The process according to claim 1, wherein the cyclization reaction in step 3 is carried out in a binary system comprising water and an organic solvent immiscible with water.

18. The process according to claim 17, wherein, after the cyclization reaction, the organic phase is removed by liquid-liquid separation and an aqueous solution of 3-hydroxytetrahydrofuran (3) is recovered.

19. The process according to claim 18, wherein the removal of the organic phase by liquid-liquid separation is carried out at a temperature not higher than 30° C.

20. The process according to claim 1, wherein the aqueous solution of 3-hydroxytetrahydrofuran (3) obtained in step 3 is washed with an organic solvent immiscible with water.

21. The process according to claim 20, wherein the washing is carried out at a temperature not higher than 30° C.

22. The process according to claim 1, wherein the extraction procedure in step 4 is carried out at a temperature not lower than 40° C.

23. The process according to claim 1, wherein the extraction procedure in step 4 is carried out under acidic to neutral conditions.

24. The process according to claim 23, wherein the extraction procedure in step 4 is carried out under neutral conditions.

25. The process according to claim 23 wherein the extraction procedure in step 4 is carried out after once basifying the aqueous solution obtained in step 3 and then neutralizing the same.

26. The process according to claim 1, wherein the organic solvent immiscible with water as used in step 4 is an aromatic hydrocarbon, an acetic acid ester or a monohydric alcohol containing 4 to 8 carbon atoms.

27. The process according to claim 26, wherein the organic solvent immiscible with water as used in step 4 is an acetic acid $C_1$–$C_4$ alkyl ester.

28. The process according to claim 1, wherein, in carrying out the distillation in step 5, the solution and/or concentrate of 3-hydroxytetrahydrofuran (3) is treated with a monohydric alcohol containing 1 to 3 carbon atoms or a polyhydric alcohol containing not less than 6 carbon atoms.

29. The process according to claim 28, wherein the content of the coexisting boron compound and/or aluminum compound is reduced to not more than 10 mole percent based on 3-hydroxytetrahydrofuran (3) by treatment with a monohydric alcohol containing 1 to 3 carbon atoms.

30. The process according to claim 1, wherein, in carrying out the distillation in step 5, the solution and/or concentrate of 3-hydroxytetrahydrofuran (3) is treated by adding an acid thereto.

31. The process according to claim 1, wherein the distillation in step 5 is carried out in the presence of a base.

32. The process according to claim 31, wherein the base is an alkali metal carbonate or an alkali metal hydrogen carbonate.

33. The process according to claim 32, wherein the base is sodium hydrogen carbonate.

34. A process for producing a 4-halo-1,3-butanediol which comprises reducing a 4-halo-3-hydroxybutyric acid ester of the general formula (1):

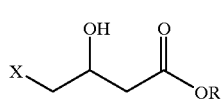

(1)

wherein R represents an ester-forming protective group and X represents a halogen atom, with a boron hydride compound and/or an aluminum hydride compound as a reducing agent in an organic solvent immiscible with water
and treating the obtained reaction mixture with an acid and water to thereby effect conversion to the corresponding 4-halo-1,3-butanediol of the general formula (2):

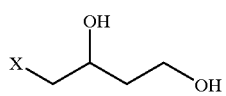

(2)

wherein X represents a halogen atom,
and at the same time giving an aqueous solution containing said compound.

35. The process according to claim 34, wherein R in the general formula (1) is an alkyl group containing 1 to 4 carbon atoms.

36. The process according to claim 34, wherein X in the general formulas (1) and (2) is chlorine, bromine or iodine.

37. The process according to claim 34, wherein the organic solvent immiscible with water is an aprotic organic solvent immiscible with water.

38. The process according to claim 37, wherein the organic solvent immiscible with water is a hydrocarbon or an acetic acid ester.

39. The process according to claim 38, wherein the organic solvent immiscible with water is toluene or an acetic acid $C_1$–$C_4$ alkyl ester.

40. The process according to claim 34, wherein the reducing agent is an alkali metal borohydride.

41. The process according to claim 40, wherein the alkali metal borohydride is sodium borohydride.

42. The process according to claim 34, wherein the reduction reaction is carried out at a temperature not lower than 40° C.

43. The process according to claim 34, wherein the reduction reaction is carried out by adding the 4-halo-3-hydroxybutyric acid ester (1) and/or the reducing agent continuously or in divided portions.

44. The process according to claim 43, wherein the reduction reaction is carried out by adding the reducing agent gradually to a solution of the 4-halo-3-hydroxybutyric acid ester (1).

45. The process according to claim 43, wherein the addition is carried out over a period not shorter than 1 hour.

46. A process for producing a 3-hydroxytetrahydrofuran of the formula (3):

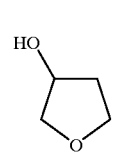

(3)

by cyclizing a 4-halo-1,3-butanediol of the general formula (2):

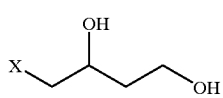

(2)

wherein X represents a halogen atom in an aqueous solution, which comprises carrying out the cyclization reaction under weakly acidic to neutral conditions.

47. The process according to claim 46, wherein the cyclization reaction is carried out at a temperature not lower than 40° C.

48. The process according to claim 47, wherein the cyclization reaction is carried out by raising the temperature to a vicinity of the boiling point of the reaction system.

49. The process according to claim 46, wherein the cyclization reaction is carried out while maintaining the pH at 2 to 7 by neutralizing the acid component generated.

50. The process according to claim 46, wherein the cyclization reaction is carried out in a binary system in which an organic solvent immiscible with water coexists.

51. The process according to claim 50, wherein, after the cyclization reaction, the organic phase is removed by liquid-liquid separation and an aqueous solution of 3-hydroxytetrahydrofuran (3) is recovered.

52. The process according to claim 51, wherein the removal of the organic phase by liquid-liquid separation is carried out at a temperature not higher than 30° C.

53. The process according to claim 46, wherein the aqueous solution of 3-hydroxytetrahydrofuran (3) obtained after the cyclization reaction is washed with an organic solvent immiscible with water.

54. The process according to claim 53, wherein the washing is carried out at a temperature not higher than 30° C.

55. A process for recovering a 3-hydroxytetrahydrofuran which comprises extracting 3-hydroxytetrahydrofuran from an aqueous solution containing 3-hydroxytetrahydrofuran with an organic solvent immiscible with water at a temperature not lower than 40° C.

56. The process according to claim 55, wherein the organic solvent immiscible with water is an aromatic hydrocarbon or an acetic acid ester.

57. The process according to claim 56, wherein the organic solvent immiscible with water is an acetic acid $C_{1-4}$ alkyl ester.

58. The process according to claim 55, wherein the extraction is carried out at a temperature not lower than 50° C.

59. A process for recovering a 3-hydroxytetrahydrofuran which comprises extracting 3-hydroxytetrahydrofuran from an aqueous solution containing 3-hydroxytetrahydrofuran with a monohydric alcohol containing 4 to 8 carbon atoms.

60. The process according to claim 59, wherein the monohydric alcohol containing 4 to 8 carbon atoms is a butanol selected from among 1-butanol, 2-butanol and isobutanol.

61. The process according to claim 59, wherein the extraction is carried out at a temperature not lower than 40° C.

62. A process for recovering a 3-hydroxytetrahydrofuran from a mixture comprising 3-hydroxytetrahydrofuran and a boron compound and/or an aluminum compound by distillation which comprises treating the mixture comprising 3-hydroxytetrahydrofuran and a boron compound and/or an aluminum compound with a monohydric alcohol containing 1 to 3 carbon atoms or a polyhydric alcohol containing not less than 6 carbon atoms in carrying out the distillation.

63. The process according to claim 62, wherein the content of the coexisting boron compound and/or aluminum compound is reduced to an amount of not more than 10 mole percent based on 3-hydroxytetrahydrofuran (3) by treatment with a monohydric alcohol containing 1 to 3 carbon atoms.

64. The process according to claim 62, wherein the solution and/or concentrate of 3-hydroxytetrahydrofuran, obtained by extraction, is treated with a monohydric alcohol containing 1 to 3 carbon atoms or a polyhydric alcohol containing not less than 6 carbon atoms.

65. A process for recovering a 3-hydroxytetrahydrofuran which comprises carrying out distillation of 3-hydroxytetrahydrofuran in the presence of a base.

66. The process according to claim 65, wherein the base is an alkali metal carbonate or an alkali metal hydrogen carbonate.

67. The process according to claim 66, wherein the base is sodium hydrogen carbonate.

* * * * *